United States Patent [19]

Walker

[11] 4,194,250
[45] Mar. 25, 1980

[54] LOAD-STABILIZING PROSTHETIC JOINT AND CONNECTING COMPONENT THEREOF

[75] Inventor: Peter S. Walker, Ridgewood, N.J.
[73] Assignee: Codman & Shurtleff, Inc., Randolph, Mass.
[21] Appl. No.: 884,777
[22] Filed: Mar. 8, 1978
[51] Int. Cl.² .............................................. A61F 1/24
[52] U.S. Cl. ...................................... 3/1.91; 128/92 C
[58] Field of Search ................................. 3/1.9–1.913; 128/92 C, 92 CA

[56] References Cited

U.S. PATENT DOCUMENTS

| | | | |
|---|---|---|---|
| 3,506,982 | 4/1970 | Steffee | 3/1.91 |
| 3,694,821 | 10/1972 | Moritz | 3/1.911 |
| 3,760,427 | 9/1973 | Schultz | 3/1.91 |
| 3,816,854 | 6/1974 | Schlein | 3/1.91 |
| 3,852,830 | 12/1974 | Marmor | 3/1.911 |
| 3,869,729 | 3/1975 | Attenborough | 3/1.91 |
| 3,879,766 | 4/1975 | Lowe et al. | 3/1.91 |
| 3,918,101 | 11/1975 | Lagrange et al. | 3/1.911 |
| 4,092,740 | 6/1978 | Eshriqui | 3/1.91 X |
| 4,106,128 | 8/1978 | Greenwald et al. | 3/1.91 |

*Primary Examiner*—Ronald L. Frinks

[57] ABSTRACT

A load-stabilizing prosthetic joint is comprised of three basic components. A first component is adapted to be associated with a first bone and has an arcuate bearing surface and a shank terminating in a headed member. A second component is adapted to be associated with a second bone adjacent the first bone and has a terminal portion with rigid walls defining an open ended socket. A third component, for connecting the first and second components, has an internal cavity and a passage communicating therewith. The third component is sufficiently flexible to permit the headed member to be passed through the pasage into the cavity to connect the first and third components. The rigid walls of the second component embrace the third component providing support therefor, and prevent the headed member from passing outwardly of the passage in use. Included on the third component is an arcuate bearing surface mating with the arcuate bearing surface of the first component, the bearing surfaces cooperating to carry the loading forces of and stabilize the joint in use.

This joint includes cooperative locking means between the second and third components to prevent their separation under lateral displacement between the first and second components.

11 Claims, 6 Drawing Figures

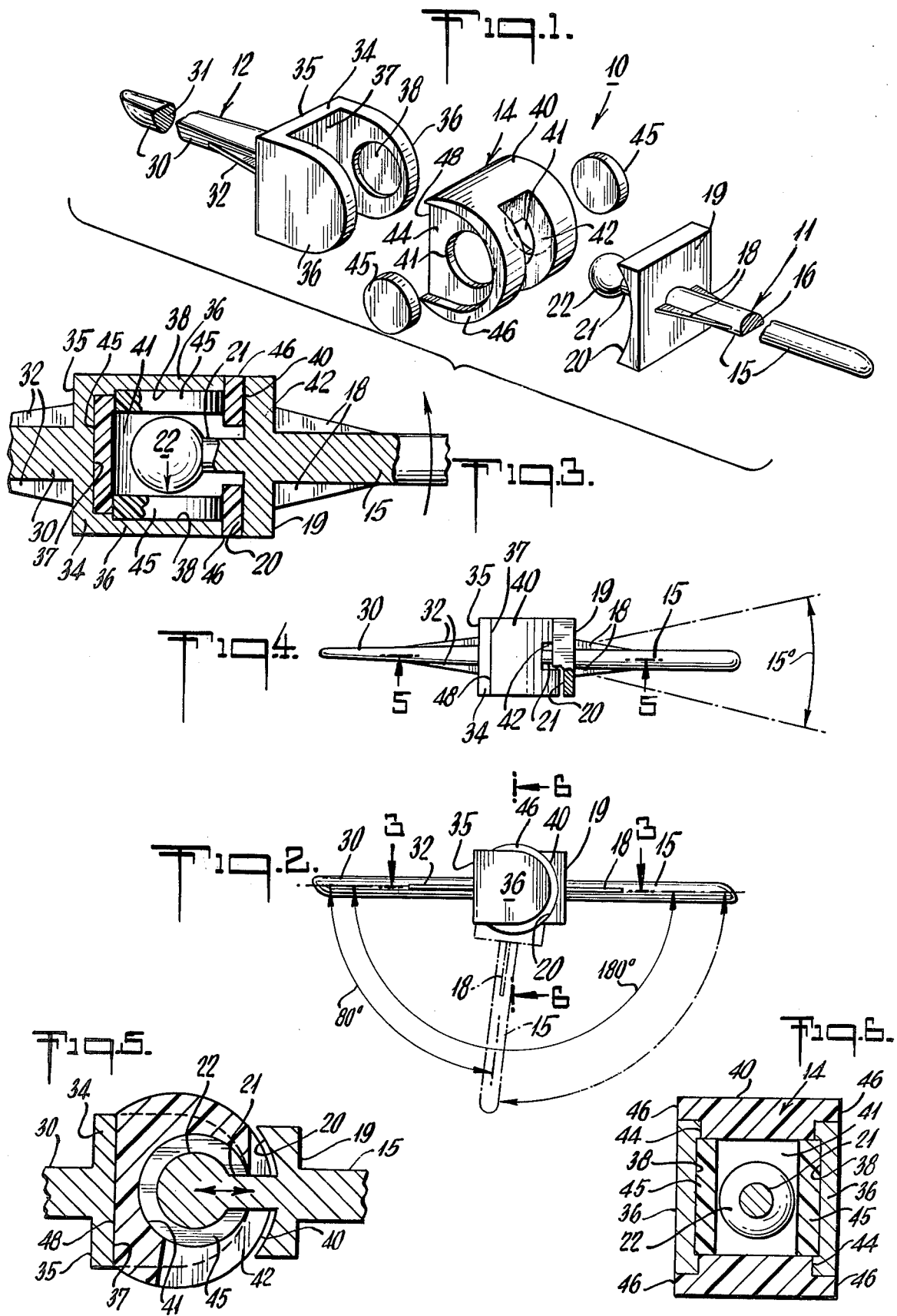

LOAD-STABILIZING PROSTHETIC JOINT AND CONNECTING COMPONENT THEREOF

BACKGROUND OF THE INVENTION

This invention relates generally to prosthetic joints and, more particularly, concerns a prosthesic joint for use as a hinge joint of the type wherein the loading forces of the joint are load-stabilized in use in the human body. This invention further relates to a prosthetic component for use in a prosthetic joint, and also to a connecting component for interconnecting two components of a prosthetic joint, especially of the load-stabilizing type.

Due to various causes, such as severe rheumatoid arthritis, for example in the metacarpophalangeal joint, it is often necessary to surgically replace the affected joint, including treatments such as resection arthroplasty. Such a surgical treatment not only relieves the discomfort and sufferings of the individual involved, but also is intended to provide a strong, stable joint which functions similarly to the natural joint which is being replaced. However, resection arthroplasty has had limited success in that no inherent stability is provided by the operation, but primarily relief of pain, and reliance is placed on the subsequent growth of soft tissues around the joint to provide any stability at all. By replacing a natural human joint with a mechanical prosthesis the individual may gain the virtual complete reuse of that joint if the prosthesis is appropriately designed.

In joints of the type wherein movement or hinge action occurs generally in one plane the commonly known prostheses which are offered for replacements have had a similar structure. For instance, the Steffee design (U.S. Pat. No. 3,506,982) for ginglymus joints employs a ball and socket for articulation. As commonly relied upon, the ball and socket configuration provides the hinging action for rotative movement with a sufficiently restrictive construction to confine the movement generally to one plane. In addition, the ball and socket design offers a construction whereupon the curved surface of the ball and the inside mating surface of the socket act as the load bearing surfaces of the joint during use, there being a substantially large available surface area over which to distribute the forces. Other similar devices are described in U.S. Pat. Nos. 3,694,821 and 3,760,427.

One of the deficiencies associated with the ball and socket construction of artificial joints is the lack of locking capacity to keep the components together. For example, in the Steffee design (noted above) the ball is snapped into the socket which has flexible lips surrounding the cavity to hold the ball. It is conceivable, and sometimes happens, that after this type of joint is implanted the components can become separated depending upon the forces which are exerted upon it. Such separation may occur because of the flexible lip structure of the socket and the general lack of any feasible and practical means to lock the ball in place in the implanted prosthesis. When dislocation of an endoprosthesis occurs it often requires another surgical operation to correct the problem.

Another deficiency in the ball and socket combination lies in the structure of the ball member itself. Generally the shank carrying the ball is slender and has a much smaller diameter than the ball it is carrying. Under severe loading forces of the joint, the ball transmits the forces along the shank for dissipation into the bone. In cases of unexpectedly large shear forces, if the ball does not become dislocated from the socket, the shank may fail and fracture thereby rendering the joint useless, thus requiring a surgical operation to either replace or repair the defective prosthesis.

Of course, it has also been known that one way to assure locking of the components of an endoprosthetic joint, while assuring rotative movement in one plane, is to pin the components together by means of an axle. Thus, instead of ball and socket articulation, the components of the prosthesis pivot around an axle thereby providing a hinged joint. Such a prosthetic joint is typified in U.S. Pat. No. 3,879,766. It has been found, however, that axle hinged joints, when cemented into the bone, generally become too rigid, thereby restricting motion and occasionally breaking; on the other hand, when such hinged joints are not cemented to the bone, the joint has occasionally produced localized areas of high stress which may cause erosion effects in the intramedullary canals. In addition, insertion of the axle, often from a side direction, to pin the two components together is not always convenient and straightforward in surgery. Depending upon the joint involved, and especially when a small joint such as one of the metacarpophalangeal finger joints is being replaced, there is very limited room in which to manipulate the axle, which produces an awkward operating procedure if such can be accomplished at all.

Another of the known prostheses which can be used as a replacement for a hinged joint is disclosed in U.S. Pat. No. 3,875,594. In that patent, a surgically implantable prosthetic joint is offered which is of a one-piece construction, molded of silicone rubber. While this type of joint replacement is flexible and eliminates the necessity of combining components together for an articulative joint, there are inherent shortcomings in this type of silicone rubber prosthesis. Primarily, there is a great reduction of strength when using silicone rubber instead of metallic components which are used in prostheses such as Steffee has disclosed. The reduced strength of the molded silicone rubber implant, in addition, limits the stability which the appropriate finger or limb is capable of subsequently developing.

As can be seen, the deficiencies in the various types of endoprosthetic devices as described above are indicative of the need for improvements in this field.

SUMMARY OF THE INVENTION

The prosthetic joint of the present invention comprises three basic components. A first component is adapted to be associated with a first bone, and has an arcuate bearing surface facing away from the first bone. A shank terminating in a headed member is included, with the headed member having a larger cross-sectional dimension than the shank in at least one plane.

A second component is adapted to be associated with a second bone adjacent to the first bone. A terminal portion is at one end of the second component facing toward the headed member of the first component, with the terminal portion having rigid wall means defining an open ended socket.

A third component connects the first and second components and has an arcuate bearing surface mating with the arcuate bearing surface of the first component. Within the third component is an internal cavity for reception of the headed member of the first component, and passage means communicates with the internal cavity. The passage means has a width dimension larger than the cross-sectional dimension of the shank, but smaller than the larger cross-sectional dimension of the headed member; the third component is sufficiently flexible to permit the headed member to pass through the passage means and into the internal cavity. To prevent the headed member from passing outwardly of the passage in use, the rigid wall means on the second component embraces the third-component providing support therefor. The mating arcuate bearing surfaces on the first and third components cooperate to carry the loading forces of and stabilize the joint in use.

In the preferred embodiment of the prosthetic joint of this invention, the arcuate bearing surface of the first component is concave, while the arcuate bearing surface of the third component is convex. This embodiment further includes locking means associated with both the second and third components to lock those two components together while reducing or eliminating the possibilities of their separating when the joint is in use.

Another aspect of the present invention is a prosthetic component of a joint of the type including at least two components, one of which is pivotally attached in the joint, and wherein the loading forces of that joint in use are carried by mating bearing surfaces of two components of the joint. Comprising this prosthetic component is a stem for insertion in the intramedullary canal of a bone, and an arcuate bearing surface at one end of the stem and facing away therefrom. This surface is for mating with another bearing surface in the joint to carry the loading forces. A shank is included on this component, and terminates in a headed member, the headed member having a larger cross-sectional dimension than the shank in at least one plane. The headed member provides pivotal attachment of the component in the formed joint.

A further aspect of the present invention is a connecting component for interconnecting two components of a prosthetic joint together. Comprising the connecting component is a substantially cylindrically shaped, flexible body having a convex peripheral surface and two flat sides. An internal cavity is within the body, and passage means communicates with the internal cavity from the peripheral surface for accomodating means to connect the first of the joint components to the connecting component. Means on each flat side provides engagement to the second of the joint components so that, in use, the connecting component interconnects the first and second joint components.

In accordance with this invention, the deficiencies of the known prosthetic joints, as discussed above, are overcome, and further advantages are offered as well. The prosthetic joint of this invention is appropriately designed to offer the advantage of increased strength of the joint, allowing the muscles and soft tissues to theoretically provide normal strength and motion to the respective joint being replaced. In its primary application, this new prosthesis is intended to provide a joint in which rotative movement is generally in one plane, such as flexionextension of a finger or elbow joint or the like.

Another advantageous feature of this new prosthetic joint is the locking together of the components which form the joint to prevent subsequent dislocation of the joint after the implant is made. This locking is accomplished by the novel design, compatibility and structure of the components which comprise the joint. Of course, an implanted joint in which the components thereof remain together even under sever loading forces is highly desirable. In one embodiment of the present invention, means to lock the components together is provided to maintain them as such even when motion contrary to the primary plane of the rotation is experienced.

A further advantage of this new prosthetic joint is its ability to stabilize the joint when it is under a loading force such as the compression experienced in pinching, gripping, and the like. Under these circumstances, the components of the new prosthetic joint are designed to minimize lateral moments which could arise in conjunction with lateral forces on the respective stems. This is desirable since the joint can withstand significantly greater true compressive forces than it can lateral forces. This feature reduces the possibilities of breakage of the joint when it is in compression should there be any unexpected lateral forces on the stems.

A still further advantage of the prosthetic joint of the present invention is the elimination of axle pinning which is prevalent in many of the known and used prostheses. The prosthestic joint of the present invention, while composed of multiple components, is easily and readily assembled and inserted into the patient; as a result of the novel design and structure of the components no external axle or the like pinning is required to securely maintain the parts together. Secure attachment of the components is achieved by internal locking means that needs no additional devices to provide such locking. As a result, the method of inserting and assembling this new prosthesis in a human body is not only initially convenient, but decreases, significantly, the likelihood that dislocation of the joint will occur subsequently when in actual use.

BRIEF DESCRIPTION OF THE DRAWINGS

FIG. 1 is an exploded perspective view showing the preferred embodiment of the prosthetic joint of the present invention;

FIG. 2 is a side elevation view of the assembled joint shown in the compressive loading position with the range of rotative movement of one component illustrated by broken lines;

FIG. 3 is an enlarged cross-sectional view taken along lines 3—3 of FIG. 2;

FIG. 4 is a plan view of the unloaded, assembled prosthetic joint depicting the limited lateral movement thereof in broken lines;

FIG. 5 is an enlarged cross-sectional view taken along lines 5—5 of FIG. 4; and

FIG. 6 is an enlarged cross-sectional view taken along lines 6—6 of FIG. 2.

DETAILED DESCRIPTION

Adverting to the drawings, particularly FIG. 1, there is illustrated a preferred embodiment of a load-stabilizing prosthetic joint with the components of that joint shown in an exploded view. While at times the joint being discussed may be referred to as the metacarpophalangeal joint for sake of example or clarity, it is understood that this prosthetic joint is not so limited in its application and may pertain to other similarly acting joints. There is shown in FIG. 1 a prosthetic joint 10 which is intended to be implanted in a human body. This joint is particularly applicable as a mechanical replacement for a hinged type joint which has rotative movement generally in one plane, such as the elbow and various finger joints. Three basic components make up this joint: a first component 11, such as a phalangeal component; a second component 12, such as a metacarpal component; and a third component 14, to interconnect the first and second components and provide a unitary structure. Plugs 45 are employed in this embodiment for locking purposes in connection with the second and third components to be hereinafter discussed in greater detail.

Turning to first component 11, it includes an elongated, slender stem 15, preferably having a somewhat roughened finish in order to provide a better grip for the cement. The stem is to be inserted into the intramedullary canal of a bone, such as one of the phalangeal bones of the hand or finger, which has been surgically prepared to receive the stem. Depending upon the particular joint which prosthetic joint 10 is replacing, the length, cross-sectional shape and contour of stem 15 may vary; in addition, characteristics of bones of different persons into which the prosthesis is introduced dictate a variety of stem differences. When used in the phalangeal bone, the stem is preferentially straight and has a cross-sectional shape in the form of a hemicircle 16 to conform to the normal bone canal shape and to prevent rotation when cemented in place. At one end of stem 15 a pair of thin, tapered or triangular fins 18 are provided. Fins 18 are located on opposite sides of stem 15 and extend in tapering fashion inwards until they merge into the stem towards the opposite end of the stem. Fins 18 fit into small slots cut into ends of the prepared bone, assisting in properly locating the stems in the bone canal and providing for rotational stability after the stem is inserted into the canal. Additionally, the fins may have holes therethrough as an alternative or compliment to cement fixation; bone and/or fibrous tissue grow into these holes to provide a stable locking effect.

A platform 19 abuts against stem 15 at the same end thereof where fins 18 are located so that the fins taper away from the platform. The surface of platform 19 facing stem 15 is flat and rests against the bone to support the first component in use. In this embodiment the surface 20 of the platform facing away from stem 15 is a curved or concave arcuate bearing surface for carrying the loading forces of the joint in use in conjunction with a surface of the third component. Arcuate bearing surface 20 is formed preferentially with a concave curvature having a radius to substantially mate with a convex bearing surface on the third component as discussed herein.

To provide means to allow this first component to pivot in the formed joint a shank 21 is located thereon. This shank is generally a short bar or rod which is attached to or integrally formed as part of the first component. At a terminal end of the shank is a headed member, which in this instance is a substantially spherical ball 22. Ball 22 has a larger cross-sectional dimension than the shank; of course, other headed members may be employed, such as T-bars or hammer heads or the like as long as the head has a larger cross-section than the shank in at least one plane. Desirably, shank 21 projects outwardly from the arcuate bearing surface so that pivotal attachment of the first component can be conveniently accomplished in the formed joint; in this regard projecting shank 21 extends from the center point of arcuate surface 20 and preferably along the axis of the stem to allow the stem to pivot along the same axis.

Included on the second component is an elongated, slender stem 30 which is similar in many respects to stem 15 of the first component; stem 30 is to be inserted in the intramedullary canal of a second bone adjacent the first bone so that an articulative joint can be formed. This second bone, for example, may be the metacarpal bone forming one member of the metacarpophalangeal joint, and it is also prepared during surgery to receive stem 30 of the second component. While stem 30 may have variations in its length, cross-sectional shape and contour, when used as a metacarpal component its cross-section preferably is shaped in a triangle 31 with rounded edges for conformity with the shape of the normal bone canal and to prevent twisting in the fixation cement. Thin, tapered or triangular fins 32, similar to fins 18 on the first component, are positioned one on each side of stem 30 at one end thereof. Fins 32 also extend in tapering fashion inwards until they merge into stem 30 towards the opposite end of that stem.

At the end of stem 30 where the fins are located is a platform or terminal portion 34 away from which fins 32 taper. Terminal portion 34 has a flat back surface 35 which abuts against stem 30 and is the surface which rests upon the bone to provide support and location. In the formed joint terminal portion 34 faces towards ball 22 on the first component, and has a pair of rigid walls 36 extending therefrom. Walls 36 are spaced apart from each other and collectively define an open ended socket therebetween. For maximum strength, rigid walls 36 are preferentially integrally formed with the terminal portion such as a unitary U-shape structure; strength is important in these walls since they assist in transmitting and dissipating the loading forces of the joint in use. The peripheral edges of the rigid walls may be rounded, as shown, squared or otherwise shaped, as desired. The surface 37 of terminal portion 34 opposite stem 30 between rigid walls 36 is preferably a flat surface against which the third component may locate in the formed joint for additional support therefor.

In the interior facing surface of each of rigid walls 36 is a locking indentation 38. Indentation 38 may be a hole, depression, relief or the like which acts to receive a protuberance from the third component whereby the fitting arrangement of the indentation and the protuberance provides substantial locking of the components together. Size and shape of locking indentation 38 is not critical and can be included in most any way which will accommodate a mating protuberative member of the third component. Preferably, however, each indentation 38 is a circular depression slightly below the interior facing surface of rigid wall 36, and does not cause removal of a large amount of wall material which would compromise the strength of the rigid wall.

Both the first and second components are preferably made of metal such as cobalt-chrome alloy, medical grade stainless steel, and medical grade titanium alloy, but other metallic or rigid plastic materials suitable for use internal to the human body may also be used. Metal components are preferred because they provide the strength to the joint and wear well over extended periods of time.

Third component 14 is a substantially cylindrically shaped flexible body having a convex arcuate bearing surface 40 around its periphery; convex surface 40 has a radius of curvature to mate with the concave bearing surface 20 on the first component to carry the loading forces of the joint in use. Convex peripheral surface 40 is generally smoothly finished so that the concave bearing surface 20 can slide freely thereover when the joint is flexed. Within the body of the third component is an internal cavity 41, in this instance a hole from side to side through the body, which is sufficiently large to receive ball 22 at the end of shank 21 on the first component. Desirably, internal cavity 41 is somewhat larger than the ball diameter of the first component so that ball 22 has some free play and a somewhat spacious environment at least along the axial direction of movement as hereinafter discussed. Around a portion of the peripheral surface 40 and extending therethrough is a passage, in this instance a slot 42, which communicates with internal cavity 41. Slot 42 has a width dimension larger than the cross-sectional dimension of shank 21, but smaller than the larger cross-sectional dimension of ball 22. Inasmuch as the body of the third component 14 is flexible this permits the slot to be widened during assembly of the joint, and ball 22 to pass therethrough, since there are no restraints on the sides of the body. Thus, after passing through slot 42, ball 22 settles in internal cavity 41 with shank 21 extending out through slot 42 thereby providing pivotal attachment of the first component to the third component. The slot, extending circumferentially around the periphery of the body, is sufficiently long and positioned to allow the first component to pivotally rotate in one plane relative to the second and third components (see FIG. 2) and thereby vary the subtending angle between the axes of the first and second components.

On opposite sides of the third component 14 are flat surfaces each of which have a recess 44 therein. Recess 44 is shaped to snugly fit over rigid wall 36 defining the socket of the second component. Recess 44 is formed in each flat side so that it is bordered by an open ended flange 46 which is the edge portion around peripheral surface 40. The open edge is a section of flange 46 which has been removed so that the third component can locate snugly over rigid wall 36. When the second and third components are assembled rigid walls 36 embrace the third component in recesses 44, provide support and lock the two components together especially eliminating rotative movement between the two components. Significantly, this locking and embracing effect acts as a restraint on the flexible body to prevent ball 22 from passing outwardly of slot 42 when the joint is in use. In addition to arcuate bearing surfaces 20 and 40 flanges 46 and rigid walls 36 assist in carrying the loading forces of the joint thereby providing more strength thereto. For more compactness in the joint and to help distribute the loading forces carried by the joint over a greater dissipation area, portion 48 of the body facing the socket walls 36 preferably is flat. In the assembled joint, flat portion 48 of the third component mates with flat surface 37 of the second component. The open end of recess 44 is aligned with flat portion 48 so that the most advantageous fit of the components can be achieved.

The natural forces which the prosthetic joint of the present invention experiences when implanted are compressive, and together with the developed fibrous capsule around the joint and the prosthetic design, the joint is kept together. However, if lateral motion of any of the stemmed components is excessive and is not accompanied by compression, the third component 14 may tend to separate at one side away from rigid wall 36. To overcome this possible occurrence, locking plugs, substantially the same diameter as hole 41, are press fit into the holes at the recessed portions of the sides, and project slightly to provide a protuberative effect. In addition, plugs 45 and indentations 38 in walls 36 of the socket of the second component are sized so that the projecting portion of the plugs fits into the indentations upon the joining of the two components, thereby providing a further locking effect thereof. Other protuberances for locking purposes may be employed on the third component 14 as long as the protuberance mates compatibly with the indentation to produce the desired locking feature; in this respect, the protuberance may be provided by adding separate elements or parts to the third component, such as plugs 45 in the embodiment being described, or the protuberance may be integrally formed in the third component. Furthermore, since the desired result is to lock as efficiently and strongly as possible components two and three together, the locking means on each is meant to include a protuberance on the second component and a mating indentation or the like on the third component, and other readily devisable techniques to achieve the locking feature.

Third or connecting component 14, and locking plugs 45 in this embodiment, are made of a flexible material, preferably a bio-compatible, high wear, plastic material, such as high molecular weight polyethylene, for example, although other similar materials may be used.

Referring to FIGS. 2 and 3, the prosthetic joint of FIG. 1 is shown fully assembled and in the loaded position, i.e., the compressive forces exerted by gripping, pinching and the like forces the mating arcuate bearing surfaces 20 and 40 of components one and three into engagement. It can be seen that when the arcuate bearing surfaces are engaged, there is no contact of ball 22 to the walls surrounding internal cavity 41, thus assuring that the ball does not carry any loading forces of the joint. Due to the engaged arcuate surfaces, the compressive loading forces are carried by concave surface 20 and convex surface 40 with virtually no rotative movement due to lateral forces on stem 15. This bearing surface configuration also provides considerable support to shearing forces in the vertical direction, as well as rotative torques. Regarding shear forces in the lateral direction, under normal use they are minimally experienced because of the arcuate bearing surfaces; however, any excessive lateral moments due to lateral force on the stems or lateral forces experienced when the joint is not in full compression (no engagement of the arcuate bearing surfaces) are handled by ball 22 being urged against plugs 45 thereby tightening the engagement of the plug into locking indentation 38 (as noted by the arrows in FIG. 3). This, of course, maintains the components in a locked position to not readily separate even under excessive lateral forces. FIG. 3 clearly illustrates ball 22 inside internal cavity 41 of the third component with the relationship of size among ball 22, shank 21 and slot 42. This view also shows the embracing effect of rigid walls 36 about the third component with the result that the flexibility of the third component is restrained to prevent ball 22 from passing outwardly of slot 42 in the assembled joint. It is also noted in this drawing that flat surface 37 of component two and flat portion 48 of component three are flatly engaged at the same time that rigid walls 36 are bottomed against flanges 46 bordering recesses 44. While this is desirable for best dissipation of loading forces, due to manufacturing tolerances, walls 36, for example, may not be completely seated in recesses 44 when the aforementioned flat surfaces of the components are in engagement, or vice versa.

FIG. 2 shows the range of pivotal, rotative movement of the first component by the broken line illustration. As this drawing is representative of a metacarpophalangeal joint, typically, the slot in the third component is positioned and is sufficiently long to allow the first component to have a range of pivotal rotation in the formed joint. This range permits the first component to become hyperextended so that the subtending angle between the axes of the first and second components is at least 180°, and then to pivotally rotate to reduce the subtending angle to about 80°. Of course, the degree of rotative movement provided by the prosthesis depends upon the type of joint being replaced.

Turning now to FIGS. 4 and 5 wherein the assembled joint is illustrated in the uncompressed condition, it can be seen that respective arcuate bearing surfaces 20 and 40 are not in engagement, such as when the joint is relaxed. In this view the mating radii of curvature of the bearing surfaces are most readily perceived. Due to the size of internal cavity 41, ball 22 therein has room to move slightly along an axial plane in addition to its pivotal features. This is depicted by the arrows in FIG. 5; while there is room for axial play, however, ball 22 is still restrained from passing out through the slot. As a result, this relaxation of the uncompressed or unloaded joint eliminates excess rigidity in the joint, and provides some lateral freedom of motion, e.g., up to about 15°, such as indicated in FIG. 4. FIG. 5 also depicts the positioning and typical length of slot 42 which is used, for instance, in the metacarpophalangeal joint. This slot around a portion of the peripheral surface of the third component provides the angular rotation of the first component relative to the second component as described above.

In FIG. 6, rigid walls 36 are shown lockingly embracing third component 14, each wall being snugly engaged in recess 44 adapted to receive the same, and bordered by flanges 46 at the edges of peripheral surface 40. Locking plugs 45 are press fit into the ends of hole 41 and protrude slightly beyond the plane of recess 44. This protrusion allows the plugs to snap into mating indentations 38 in walls 36 to assure positive locking of the components upon assembly. This illustrates that any lateral movement of component one relative to components two and three will direct ball 22 tightly against one of locking plugs 45 thereby increasing the locking effect provided by the protuberance-indentation combination.

To insert and assemble the prosthetic joint of the present invention into a human body to replace, for example, a metacarpophalengeal joint, the stems 15 and 30 of the first and second components are introduced into the intramedullary canal of the phalangeal bone and the metacarpal bone, respectively, prepared to receive the same; generally the fins 18 and 32 of each stem are nestled into slots cut into the abutting surface of the bone. Ball 22 atop shank 21 of the first component 11 is inserted into and through slot 42 in the connecting component 14. Then, the third or connecting component 14, with the first component 11 attached thereto, is pressed between rigid walls 36 forming the socket of second component 12 with recesses 44 snugly fitting thereover. This connection mates the convex peripheral surface 40 of the third component 14 with the concave surface 20 of the first component 11, and locks the components together. Plugs 45 or protuberances are already preassembled into the recessed sides of the third component 14 to assure more positive component locking. The order of the above steps is generally not critical; for instance, ball 22 may be inserted through slot 42 to connect the first component 11 to third component 14 before the former is inserted into the bone canal.

Thus, it is apparent that there has been provided in accordance with the invention a prosthetic joint and components for such a joint that fully satisfy the aims, advantages and aspects as set forth above. While the invention has been described in connection with specific embodiments thereof, the plenary invention is intended to embrace all such alternatives, modifications and variations which will be apparent to those skilled in the art in view of the foregoing description and as fall within the broadest scope and spirit of the described invention.

I claim:

1. A prosthetic joint comprising: a first component having a stem for insertion in the intramedullary canal of a first bone, said first component having an arcuate bearing surface facing away from said stem, a shank projecting outwardly from said arcuate bearing surface and having a headed member thereon, said headed member having a larger cross-sectional dimension than said shank in at least one plane; a second component having a stem for insertion in the intramedullary canal of a second bone adjacent to said first bone, said second component having a terminal portion at one end facing toward said headed member, said terminal portion having a pair of rigid walls spaced from one another and collectively defining therebetween an open ended socket; and a third component for connecting said first and second components, means defining an internal cavity within said third component for reception of said headed member, a slot in said third component communicating with said cavity, said slot having a width dimension larger than the cross-sectional dimension of said shank but smaller than said larger cross-sectional dimension of said headed member, said third component being sufficiently flexible to permit said headed member to pass through said slot and into said internal cavity, said rigid walls on said second component embracing said third component and providing support therefor to prevent said headed member from passing outwardly of said slot in use, said first component adapted to have lateral rocking movement with respect to said connected second and third components, and an arcuate bearing surface on said third component mating with the arcuate bearing surface on said first component, said bearing surfaces cooperating to carry the loading forces of and stabilize said joint in use, said joint including cooperative locking means between said second and third components responsive to contact by said headed member upon lateral displacement between said first and connected second and third components for preventing separation of said second and third components.

2. A prosthetic joint as defined in claim 1 wherein said arcuate bearing surface of said first component is concave and said arcuate bearing surface of said third component is convex.

3. A prosthetic joint as defined in claim 2 wherein said third component is substantially cylindrically shaped with its peripheral surface being the convex arcuate bearing surface.

4. A prosthetic joint as defined in claim 3 wherein said substantially cylindrically shaped third component includes a flat portion thereon for mating flatly with said terminal portion in the socket of said second component.

5. A prosthetic joint as defined in claim 1 wherein said stem of said first component has a cross-section thereof in the shape of a hemicircle, and wherein said stem of said second component has a cross-section thereof in the shape of a triangle.

6. A prosthetic joint as defined in claim 1 wherein said slot in said third component is formed to allow said first component to pivotally rotate in one plane relative to said second component and thereby vary the subtending angle between the axes of said first and second components.

7. A prosthetic joint as defined in claim 1 wherein said first and second components are formed of metal, and said third component is formed of plastic, all materials being bio-compatible for use in the human body.

8. A prosthetic joint comprising: a first component adapted to be associated with a first bone, said component having an arcuate bearing surface facing away from said first bone, said first component having a shank terminating in a headed member, said headed member having a larger cross-sectional dimension than said shank in at least one plane; a second component adapted to be associated with a second bone adjacent to said first bone, said second component having a terminal portion at one end facing toward said headed member, said terminal portion having rigid wall means defining an open ended socket; and a third component for connecting said first and second components, an internal cavity within said third component for reception of said headed member, passage means in said third component communicating with said cavity, said passage means having a width dimension larger than the cross-sectional dimension of said shank but smaller than said larger cross-sectional dimension of said headed member, said third component being sufficiently flexible to permit said headed member to pass through said passage means and into said internal cavity, said rigid wall means on said second component embracing said third component and providing support therefor to prevent said headed member from passing outwardly of said passage means in use, said first component adapted to have lateral rocking movement with respect to said connected second and third components, and an arcuate bearing surface on said third component mating with the arcuate bearing surface on said first component, said bearing surfaces cooperating to carry the loading forces of and stabilize said joint in use, said joint including cooperative locking means between said second and third components responsive to contact by said headed member upon lateral displacement between said first and connected second and third components for preventing separation of said second and third components.

9. A prosthetic joint comprising:
a first component having a stem for insertion in the intramedullary canal of a first bone, said first component having a concave arcuate bearing surface facing away from said stem, a shank projecting outwardly from said bearing surface and having a headed member thereon, said headed member having a larger cross-sectional dimension than said shank in at least one plane, said stem of said first component having a pair of thin, tapered fins, each on opposite sides thereof and being tapered inwards until they merge into said stem away from said bearing surface;

a second component having a stem for insertion in the intramedullary canal of a second bone adjacent to said first bone, said second component having a terminal portion at one end facing toward said headed member, said terminal portion having a pair of rigid walls spaced from one another and collectively defining therebetween an open ended socket, a locking indentation in the interior facing surface of each of said walls, said stem of said second component having a pair of thin, tapered fins, each on opposite sides thereof and extending from said terminal portion and being tapered inwards until they merge into said stem of said second component away from said terminal portion;

and a third component for connecting said first and second components, means defining an internal cavity within said third component for reception of said headed member, a slot in said third component communicating with said cavity, said slot having a width dimension larger than the cross-sectional dimension of said shank but smaller than said larger cross-sectional dimension of said headed member, said third component being sufficiently flexible to permit said headed member to pass through said slot and into said internal cavity, said slot being sufficiently long and positioned to allow said first component to pivotally rotate in one plane relative to said second component and thereby vary the subtending angle between the axes of said first and second components, said third component including a locking recess on opposite sides thereof, each recess being shaped to snugly locate over the walls of said socket to substantially eliminate rotative movement of said third component relative to said second component, said third component including protuberative locking means on opposite sides thereof, each of said protuberances being sized to be received in said indentations to provide locking of said second and third components, said rigid walls lockingly embracing said third component in said recesses and providing support therefor to prevent said headed member from passing outwardly of said slot in use, said first component adapted to have lateral rocking movement with respect to said connected second and third components, said third component being substantially cylindrically shaped with its peripheral surface being a convex arcuate bearing surface mating with said concave arcuate bearing surface on said first component, one portion on the periphery of said third component being a flat surface for mating flatly with said terminal portion in the socket of said second component, said bearing surfaces cooperating to carry the loading forces of and stabilize said joint in use, said protuberative locking means being responsive to contact by said headed member upon lateral displacement between said first and connected second and third components to urge said protuberative means into tighter locking effect with said indentations for preventing separation of said second and third components.

10. A prosthetic joint comprising: a first component having a stem for insertion in the intramedullary canal of a first bone, said first component having an arcuate bearing surface facing away from said stem, a shank projecting outwardly from said arcuate bearing surface and having a headed member thereon, said headed member having a larger cross-sectional dimension than said shank in at least one plane; a second component having a stem for insertion in the intramedullary canal of a second bone adjacent to said first bone, said second component having a terminal portion at one end facing toward said headed member, said terminal portion having a pair of rigid walls spaced from one another and collectively defining therebetween an open ended socket; and a third component for connecting said first and second components, means defining an internal cavity within said third component for reception of said headed member, a slot in said third component communicating with said cavity, said slot having a width dimension larger than the cross-sectional dimension of said shank but smaller than said larger cross-sectional dimension of said headed member, said third component being sufficiently flexible to permit said headed member to pass through said slot and into said internal cavity, said rigid walls on said second component embracing said third component and providing support therefor to prevent said headed member from passing outwardly of said slot in use, an arcuate bearing surface on said third component mating with the arcuate bearing surface on said first component, said bearing surfaces cooperating to carry the loading forces of and stabilize said joint in use, said third component including a recess on opposite sides thereof, each recess being shaped to locate over a wall of said socket to provide a snug fit, said rigid walls being positioned in said recesses to substantially eliminate rotative movement of said third component relative to said second component in said joint, said socket of said second component including an indentation in the interior facing surface of each of said walls, and said third component including a plug being press fit into each recessed side thereof and projecting outwardly from said recessed surface to provide a protuberative effect, each plug being sized to be received in said respective indentations to provide locking of said second and third components.

11. A connecting component for interconnecting two components of a prosthetic joint together, the first of said joint components comprising means for pivotal attachment in said joint, the second of said joint components comprising a pair of rigid walls spaced from one another and collectively defining therebetween an open ended socket, said connecting component comprising: a substantially cylindrically shaped, flexible body having a convex peripheral surface and two flat sides, said body including a flat surface on the peripheral surface thereof; a hole defining an internal cavity completely through said body and extending from side to side; a slot extending circumferentially around a portion of said convex peripheral surface and communicating with said internal cavity for accommodating said pivotal attachment means of said first joint component; and a recess in each of said sides, each recess being bordered by an open-ended flange, said flange being the edge portion of said convex peripheral surface with a section thereof removed to place said open-end in alignment with said flat peripheral surface, each recess being shaped to provide a snug fit with said walls whereby said recesses and flanges cooperate with said walls for snugly attaching said connecting component to said second joint component, at least one of said recesses including a plug being press fit therein and projecting outwardly from the surface of said recess to provide a protuberative effect and for locking said connecting component to said second joint component.

* * * * *